US008795210B2

(12) United States Patent
Talish et al.

(10) Patent No.: US 8,795,210 B2

(45) Date of Patent: Aug. 5, 2014

(54) SYSTEM AND METHOD FOR A LOW PROFILE VIBRATING PLATE

(75) Inventors: Roger J. Talish, Hillsborough, NJ (US); Titi Trandafir, S. Plainfield, NJ (US)

(73) Assignee: American Medical Innovations, L.L.C., Fort Myers, FL (US)

( * ) Notice: Subject to any disclaimer, the term of this patent is extended or adjusted under 35 U.S.C. 154(b) by 1607 days.

(21) Appl. No.: 11/827,066

(22) Filed: Jul. 10, 2007

(65) Prior Publication Data

US 2008/0015477 A1 Jan. 17, 2008

Related U.S. Application Data

(60) Provisional application No. 60/830,286, filed on Jul. 11, 2006.

(51) Int. Cl.

*A61H 1/00* (2006.01)
*A61F 5/14* (2006.01)

(52) U.S. Cl.

USPC .................................. 601/78; 601/46; 36/141

(58) Field of Classification Search

USPC ......... 601/46, 49, 51, 66, 78–83; 36/11.5, 97, 36/141; 335/231, 235, 252; 310/12, 24, 27

See application file for complete search history.

(56) References Cited

U.S. PATENT DOCUMENTS 1,125,931 A 1/1915 Roche
1,945,675 A 2/1934 Binney
2,193,978 A * 3/1940 Miller ............................. 601/80
2,345,439 A 3/1944 Tompkins
2,779,328 A 1/1957 Grossi
2,845,063 A 7/1958 Allen
2,902,993 A 9/1959 Wagner
2,916,745 A 12/1959 Lesk et al.
3,134,451 A 5/1964 Hanssen
3,193,034 A 7/1965 Hutchinson et el.
3,304,036 A 2/1967 Davis
3,304,449 A 2/1967 Pohlman et at.
3,499,437 A 3/1970 Balamuth
3,581,739 A 6/1971 Brandt et al.
3,593,239 A * 7/1971 Hofman ........................ 335/231
3,760,799 A 9/1973 Crowson (Continued)

FOREIGN PATENT DOCUMENTS

AU 667113 7/1996
AU 2006226886 3/2011

(Continued)

OTHER PUBLICATIONS

Holmlund et al., "Mechanical impedance of the human body in vertical direction", Applied Ergonomics, Elsevier Science Ltd. (2000).

(Continued)

*Primary Examiner* — Kristen Matter

(74) *Attorney, Agent, or Firm* — Malloy & Malloy, P.L.

(57) ABSTRACT

A wearable medical treatment system and method are provided for the treatment of tissue ailments and/or conditions including vascular disease, deep vein thrombosis, orthostatic intolerance, reduced blood flow, weak bone structure, orthostatic hypotension, or other conditions, using a vibrating plate. The wearable system and method use magnetic layers to generate magnetic fields to provide vertical and/or horizontal vibrational motion to a platform, thus allowing the system to have a low profile.

24 Claims, 11 Drawing Sheets

(56) References Cited

U.S. PATENT DOCUMENTS

| | | | | | |
|---|---|---|---|---|---|
| 3,762,402 | A | * | 10/1973 | Abramovitz | 601/65 |
| 3,765,407 | A | | 10/1973 | Prince | |
| 3,767,195 | A | | 10/1973 | Dimick | |
| 3,841,320 | A | | 10/1974 | Brown, Jr. | |
| 3,890,953 | A | | 6/1975 | Kraus et al. | |
| 3,911,907 | A | | 10/1975 | Smith, Jr. | |
| 3,961,380 | A | | 6/1976 | Garr | |
| 4,013,069 | A | | 3/1977 | Hasty | |
| 4,105,017 | A | | 8/1978 | Ryaby et al. | |
| 4,232,661 | A | | 11/1980 | Christensen | |
| 4,266,532 | A | | 5/1981 | Ryaby et al. | |
| 4,266,533 | A | | 5/1981 | Ryaby et al. | |
| 4,315,503 | A | | 2/1982 | Ryaby et al. | |
| 4,326,506 | A | | 4/1982 | Kawabata | |
| 4,358,105 | A | | 11/1982 | Sweeney, Jr. | |
| 4,369,537 | A | * | 1/1983 | Midgley | 12/142 RS |
| 4,381,040 | A | | 4/1983 | Brouwer | |
| D269,305 | S | | 6/1983 | Nakao et al. | |
| 4,446,586 | A | | 5/1984 | Reed et al. | |
| 4,452,326 | A | | 6/1984 | Hanssen et al. | |
| 4,530,360 | A | | 7/1985 | Duarte | |
| 4,570,927 | A | | 2/1986 | Petrofsky et al. | |
| 4,669,483 | A | | 6/1987 | Hepp et al. | |
| 4,687,195 | A | | 8/1987 | Potts | |
| 4,697,581 | A | * | 10/1987 | Endo et al. | 601/78 |
| 4,710,655 | A | | 12/1987 | Masaki | |
| 4,750,574 | A | | 6/1988 | Williams | |
| 4,782,822 | A | | 11/1988 | Ricken | |
| 4,787,888 | A | | 11/1988 | Fox | |
| 4,788,968 | A | | 12/1988 | Rudashevsky et al. | |
| D299,787 | S | | 2/1989 | Bates | |
| 4,836,316 | A | | 6/1989 | Carnevale et al. | |
| 4,858,599 | A | | 8/1989 | Halpern et al. | |
| 4,890,953 | A | | 1/1990 | Malatesta | |
| 4,905,671 | A | | 3/1990 | Senge et al. | |
| 4,913,248 | A | | 4/1990 | Zakai | |
| 4,917,376 | A | | 4/1990 | Lo | |
| 4,927,138 | A | | 5/1990 | Ferrari | |
| 4,928,959 | A | | 5/1990 | Bassett et al. | |
| 4,986,534 | A | | 1/1991 | Meier et al. | |
| 5,000,442 | A | | 3/1991 | Dalebout et al. | |
| 5,003,965 | A | | 4/1991 | Talish et al. | |
| 5,046,484 | A | | 9/1991 | Bassett et al. | |
| 5,103,806 | A | | 4/1992 | McLeod et al. | |
| 5,107,540 | A | * | 4/1992 | Mooney et al. | 381/431 |
| 5,108,452 | A | | 4/1992 | Fallin | |
| 5,113,850 | A | * | 5/1992 | Larremore et al. | 601/46 |
| 5,133,420 | A | | 7/1992 | Smith | |
| 5,145,027 | A | | 9/1992 | Petzl et al. | |
| 5,186,162 | A | | 2/1993 | Talish et al. | |
| 5,188,095 | A | | 2/1993 | Healy | |
| 5,191,880 | A | | 3/1993 | McLeod et al. | |
| 5,211,160 | A | | 5/1993 | Talish et al. | |
| 5,255,957 | A | | 10/1993 | Opsvik et al. | |
| 5,273,028 | A | | 12/1993 | McLeod et al. | |
| 5,273,502 | A | | 12/1993 | Kelsey et al. | |
| 5,295,931 | A | | 3/1994 | Dreibelbis et al. | |
| 5,318,561 | A | | 6/1994 | McLeod et al. | |
| RE34,663 | E | | 7/1994 | Seale | |
| 5,335,188 | A | | 8/1994 | Brisson | |
| 5,336,144 | A | | 8/1994 | Rodden | |
| 5,337,757 | A | | 8/1994 | Jain et al. | |
| 5,339,804 | A | | 8/1994 | Kemp | |
| 5,351,389 | A | | 10/1994 | Erickson et al. | |
| 5,368,044 | A | | 11/1994 | Cain et al. | |
| 5,376,065 | A | | 12/1994 | McLeod et al. | |
| 5,380,269 | A | | 1/1995 | Urso | |
| 5,409,446 | A | | 4/1995 | Rattner | |
| RE34,959 | E | | 5/1995 | Potts | |
| 5,429,585 | A | | 7/1995 | Liang | |
| 5,431,612 | A | | 7/1995 | Holden | |
| 5,437,668 | A | | 8/1995 | Aronson et al. | |
| 5,466,215 | A | | 11/1995 | Lair et al. | |
| 5,468,220 | A | | 11/1995 | Sucher | |
| 5,478,306 | A | | 12/1995 | Stoner | |

| | | | | | |
|---|---|---|---|---|---|
| 5,484,388 | A | | 1/1996 | Bassett et al. | |
| 5,492,525 | A | | 2/1996 | Gibney | |
| 5,496,256 | A | | 3/1996 | Bock et al. | |
| 5,501,657 | A | | 3/1996 | Feero | |
| 5,520,612 | A | | 5/1996 | Winder et al. | |
| 5,520,614 | A | | 5/1996 | McNamara et al. | |
| 5,538,489 | A | | 7/1996 | Magid | |
| 5,556,372 | A | | 9/1996 | Talish et al. | |
| 5,578,060 | A | | 11/1996 | Pohl et al. | |
| 5,602,432 | A | * | 2/1997 | Mizutani | 310/15 |
| 5,626,554 | A | | 5/1997 | Ryaby et al. | |
| 5,702,353 | A | | 12/1997 | Guzzini et al. | |
| 5,708,236 | A | | 1/1998 | Shaanan et al. | |
| 5,716,331 | A | | 2/1998 | Chang | |
| 5,721,400 | A | | 2/1998 | Haraldsson et al. | |
| 5,730,705 | A | | 3/1998 | Talish et al. | |
| 5,741,317 | A | | 4/1998 | Ostrow | |
| 5,755,746 | A | | 5/1998 | Lifshey et al. | |
| 5,762,616 | A | | 6/1998 | Talish | |
| 5,779,600 | A | | 7/1998 | Pape | |
| 5,797,860 | A | | 8/1998 | Moriyasu | |
| 5,868,649 | A | | 2/1999 | Erickson et al. | |
| 5,871,446 | A | | 2/1999 | Wilk | |
| 5,886,302 | A | | 3/1999 | Germanton et al. | |
| 5,904,659 | A | | 5/1999 | Duarte et al. | |
| 5,910,123 | A | | 6/1999 | Wang et al. | |
| 5,913,838 | A | * | 6/1999 | Reilly | 601/58 |
| 5,957,814 | A | | 9/1999 | Eschenbach | |
| 5,971,984 | A | | 10/1999 | Taylor et al. | |
| 5,987,982 | A | | 11/1999 | Wenman et al. | |
| 5,997,490 | A | | 12/1999 | McLeod et al. | |
| 6,019,710 | A | | 2/2000 | Dalebout et al. | |
| 6,022,349 | A | | 2/2000 | McLeod et al. | |
| D421,828 | S | | 3/2000 | Malka | |
| 6,050,364 | A | | 4/2000 | Popall et al. | |
| 6,061,597 | A | | 5/2000 | Rieman et al. | |
| 6,063,046 | A | | 5/2000 | Allum | |
| 6,068,596 | A | | 5/2000 | Weth et al. | |
| 6,080,088 | A | | 6/2000 | Petersen et al. | |
| 6,086,078 | A | | 7/2000 | Ferez | |
| 6,093,135 | A | | 7/2000 | Huang | |
| 6,106,491 | A | | 8/2000 | Gianutsos | |
| 6,116,691 | A | | 9/2000 | Reece | |
| 6,119,291 | A | | 9/2000 | Osborne et al. | |
| 6,179,797 | B1 | | 1/2001 | Brotz | |
| 6,234,975 | B1 | | 5/2001 | McLeod et al. | |
| 6,258,020 | B1 | | 7/2001 | Lopez | |
| 6,346,088 | B1 | | 2/2002 | Stone et al. | |
| 6,421,935 | B1 | | 7/2002 | Bartlett | |
| 6,440,046 | B1 | | 8/2002 | Tholkes | |
| D467,407 | S | | 12/2002 | Berg et al. | |
| D471,346 | S | | 3/2003 | Bray, Jr. et al. | |
| 6,558,304 | B1 | | 5/2003 | Bardon et al. | |
| 6,561,991 | B2 | | 5/2003 | McLeod et al. | |
| 6,607,497 | B2 | | 8/2003 | McLeod et al. | |
| 6,610,021 | B1 | | 8/2003 | Bock | |
| 6,620,117 | B1 | | 9/2003 | Johnson et al. | |
| 6,632,158 | B1 | | 10/2003 | Nashner | |
| 6,656,137 | B1 | | 12/2003 | Tyldsley et al. | |
| 6,843,776 | B2 | | 1/2005 | Trandafir et al. | |
| 6,884,227 | B2 | | 4/2005 | Krompasick | |
| 6,902,320 | B2 | | 6/2005 | McKenna | |
| 6,923,773 | B2 | | 8/2005 | Leivseth et al. | |
| 7,094,211 | B2 | | 8/2006 | Krompasick | |
| 7,100,439 | B2 | | 9/2006 | Carlucci | |
| 7,108,663 | B2 | | 9/2006 | Talish et al. | |
| 7,152,345 | B2 | * | 12/2006 | Koenig | 36/136 |
| 7,166,067 | B2 | | 1/2007 | Talish et al. | |
| 7,207,954 | B2 | | 4/2007 | Trandafir et al. | |
| 7,207,955 | B2 | | 4/2007 | Krompasick | |
| 7,211,060 | B1 | * | 5/2007 | Talish et al. | 602/2 |
| 7,322,948 | B2 | | 1/2008 | Talish et al. | |
| D564,734 | S | | 3/2008 | Krompasick et al. | |
| 7,338,457 | B2 | | 3/2008 | Talish et al. | |
| 7,347,831 | B2 | * | 3/2008 | Chiu | 601/15 |
| 7,402,144 | B2 | | 7/2008 | McLeod | |
| 7,491,183 | B2 | | 2/2009 | Dalen | |
| 7,525,403 | B2 | * | 4/2009 | Kim | 335/222 |
| 7,670,304 | B2 | | 3/2010 | Kim | |

(56) References Cited

U.S. PATENT DOCUMENTS

| | | | |
|---|---|---|---|
| 7,771,375 | B2 | 8/2010 | Nishibori et al. |
| 7,942,835 | B2 | 5/2011 | Talish et al. |
| 8,043,234 | B2 | 10/2011 | Talish et al. |
| 8,114,036 | B2 | 2/2012 | Krompasick |
| 2001/0000782 | A1 | 5/2001 | Schiessl |
| 2002/0077570 | A1 | 6/2002 | McLeod et al. |
| 2002/0183662 | A1 | 12/2002 | Lu |
| 2003/0083599 | A1 | 5/2003 | Kitov |
| 2003/0090374 | A1 | 5/2003 | Quigley |
| 2004/0059331 | A1 | 3/2004 | Mullaney |
| 2004/0067833 | A1 | 4/2004 | Talish et al. |
| 2004/0068211 | A1 | 4/2004 | Leivseth et al. |
| 2004/0092848 | A1 | 5/2004 | Trandafir et al. |
| 2004/0092849 | A1 | 5/2004 | Talish |
| 2004/0260211 | A1 | 12/2004 | Maalouf |
| 2005/0026750 | A1 | 2/2005 | Oglesby et al. |
| 2005/0131319 | A1 | 6/2005 | Der Meer Guus |
| 2005/0148911 | A1 | 7/2005 | Talish et al. |
| 2005/0154334 | A1 | 7/2005 | Trandafir et al. |
| 2005/0193820 | A1 | 9/2005 | Sheljaskow et al. |
| 2005/0251068 | A1 | 11/2005 | Mor |
| 2006/0047230 | A1 | 3/2006 | Talish |
| 2006/0076816 | A1 | 4/2006 | Fujita et al. |
| 2006/0111652 | A1 | 5/2006 | McLeod |
| 2006/0155221 | A1 | 7/2006 | Kim |
| 2006/0200054 | A1 | 9/2006 | Talish et al. |
| 2006/0217640 | A1 | 9/2006 | Trandafir |
| 2006/0241528 | A1 | 10/2006 | Talish |
| 2007/0021693 | A1 | 1/2007 | Trandafir et al. |
| 2007/0027410 | A1 | 2/2007 | Cost |
| 2007/0038165 | A1 | 2/2007 | Trandafir et al. |
| 2007/0043310 | A1 | 2/2007 | Trandafir et al. |
| 2007/0055185 | A1 | 3/2007 | Trandafir et al. |
| 2007/0073196 | A1 | 3/2007 | Tanaka et al. |
| 2007/0184953 | A1 | 8/2007 | Luberski et al. |
| 2007/0213179 | A1 | 9/2007 | Trandafir |
| 2007/0219473 | A1 | 9/2007 | Talish et al. |
| 2007/0232965 | A1 | 10/2007 | Talish |
| 2007/0260161 | A1 | 11/2007 | Trandafir et al. |
| 2008/0009776 | A1 | 1/2008 | Trandafir |
| 2008/0015476 | A1 | 1/2008 | Talish et al. |
| 2008/0015477 | A1 | 1/2008 | Talish et al. |
| 2008/0139977 | A1 | 6/2008 | Talish et al. |
| 2008/0139978 | A1 | 6/2008 | Talish et al. |
| 2008/0139979 | A1 | 6/2008 | Talish et al. |
| 2008/0214971 | A1 | 9/2008 | Talish et al. |
| 2009/0062698 | A1 | 3/2009 | Einav et al. |
| 2009/0228229 | A1 | 9/2009 | Trandafir |
| 2010/0152819 | A1 | 6/2010 | McLeod |

FOREIGN PATENT DOCUMENTS

| | | | |
|---|---|---|---|
| CA | 2136012 | | 5/2004 |
| CA | 2463376 | | 1/2008 |
| CA | 2504459 | | 1/2008 |
| CA | 2531570 | | 9/2009 |
| CA | 2602040 | | 3/2013 |
| CH | 323 767 | A | 8/1957 |
| CN | ZL200380102816.5 | | 9/2008 |
| CN | ZL200710165664.3 | | 8/2011 |
| DE | 15 66 521 | A1 | 3/1971 |
| DE | 32 27 519 | A1 | 2/1983 |
| DE | 94 10 902 | U1 | 11/1995 |
| DE | 196 39 477 | A1 | 4/1998 |
| DE | 102 01 255 | A1 | 7/2003 |
| EP | 0029298 | | 5/1981 |
| EP | 0 695 559 | | 2/1996 |
| EP | 1 026 484 | | 8/2000 |
| EP | 1 400 264 | A1 | 3/2004 |
| EP | 1656921 | A1 | 5/2006 |
| EP | 1455725 | | 6/2006 |
| FR | 2 562 446 | | 10/1985 |
| FR | 2562446 | | 10/1985 |
| JP | 60150749 | | 8/1985 |
| JP | 62-72359 | | 4/1987 |
| JP | 2-60608 | | 3/1990 |
| JP | U 2-32830 | | 3/1990 |
| JP | U 4-3736 | | 1/1992 |
| JP | 04-504666 | | 8/1992 |
| JP | 5317376 | | 12/1993 |
| JP | 7507224 | | 8/1995 |
| JP | 3036291 | | 1/1997 |
| JP | 3038101 | | 6/1997 |
| JP | 11319144 | | 11/1999 |
| JP | 2000-60978 | | 2/2000 |
| JP | 3069745 | | 4/2000 |
| JP | 2001-000496 | | 1/2001 |
| JP | 2001-017493 | | 1/2001 |
| JP | 2001-070383 | | 3/2001 |
| JP | 2001-513352 | | 9/2001 |
| JP | 2001-517134 | | 10/2001 |
| JP | 2001-346846 | | 12/2001 |
| JP | 2002-153349 | | 5/2002 |
| JP | 2002-306559 | | 10/2002 |
| JP | 2002-325808 | | 11/2002 |
| JP | 2003-102801 | | 4/2003 |
| JP | 3547742 | | 4/2004 |
| JP | 2004-321665 | | 11/2004 |
| JP | 2004-337275 | | 12/2004 |
| JP | 2005-512721 | | 5/2005 |
| KR | 0225300 | | 7/1999 |
| KR | 10-0974673 | | 8/2010 |
| MX | 183314 | | 11/1996 |
| SU | 584 842 | A1 | 12/1977 |
| WO | WO 93/24092 | | 12/1993 |
| WO | WO 95/21580 | | 8/1995 |
| WO | WO 96/03104 | A | 2/1996 |
| WO | WO 02/053084 | | 7/2002 |
| WO | WO 03/030805 | | 4/2003 |
| WO | WO 03/055389 | | 7/2003 |
| WO | WO 2004/043324 | | 5/2004 |
| WO | WO 2004/096108 | A2 | 11/2004 |
| WO | WO 2004/103244 | A1 | 12/2004 |
| WO | WO 2005/000188 | A1 | 1/2005 |
| WO | WO 2005/115298 | | 12/2005 |
| WO | WO 2006/001656 | | 1/2006 |
| WO | WO 2006/023817 | | 3/2006 |
| WO | WO 2006/096662 | A1 | 9/2006 |
| WO | WO 2006/096734 | | 9/2006 |
| WO | WO 2006/096734 | A1 | 9/2006 |
| WO | WO 2006/102582 | | 9/2006 |
| WO | WO 2007/011885 | | 1/2007 |
| WO | WO 2007/015748 | | 2/2007 |
| WO | WO 2007/015856 | | 2/2007 |
| WO | WO 2007015749 | | 2/2007 |
| WO | WO 2007/103413 | | 9/2007 |
| WO | WO 2007/103414 | | 9/2007 |
| WO | WO 2007/103415 | | 9/2007 |
| WO | WO 2007/103516 | | 9/2007 |
| WO | WO 2008/008317 | | 1/2008 |
| WO | WO 2008/008340 | | 1/2008 |
| WO | WO 2008/070826 | | 6/2008 |
| WO | WO 2009/023432 | | 2/2009 |
| WO | WO 2009/073881 | | 6/2009 |
| WO | WO 2009/111561 | | 9/2009 |

OTHER PUBLICATIONS

Wei et al., "The Prediction of Seat Transmissiblity from Measures of Seat Impedance", Journal of Sound and Vibration, 214(1), pp. 121-137 (1998).

PCT International Search Report and Written Opinion for PCT/US2007/015694 dated Dec. 21, 2007.

PCT International Search Report for PCT/US2007/015732 dated Jan. 24, 2008.

PCT International Search Report (ISR) for PCT/US2006/027723, Oct. 30, 2006, European Patent Office.

Edward, V., PCT International Search Report (ISR) for PCT/US2006/008132. Jul. 2, 2006, European Patent Office.

Artikis, T., PCT International Search Report (ISR) for PCT/US2006/010753. Jul. 20, 2006, European Patent Office.

Fischer, E., PCT International Search Report (ISR) for PCT/US2006/007983. Jul. 13, 2006, European Patent Office.

(56) References Cited

OTHER PUBLICATIONS

Yu, J., International Preliminary Report on Patentability (IPRP) for PCT/US06/07983. Apr. 20, 2007, Alexandria, VA.
Fischer, E., PCT International Search Report (ISR) for PCT/US2006/027355. Oct. 26, 2006, European Patent Office.
Fischer, E., PCT International Search Report (ISR) for PCT/US2006/027832, Oct. 26, 2006, European Patent Office.
Pope, M.H. et al., "Mounting of the Transducers in Measurement of Segmental Motion of the Spine," J. Biomechanics, 1986, pp. 675-677, vol. 19, No. 8.
Jordan, J., "Good Vibrations and Strong Bones," Am. J. Physiol. Reful. Integr. Comp. Physiol., 288 (3): R555-556 (2005).
Stewart, J.M. et al., "Plantar vibration improved leg fluid . . . ," The American Journal of Phgy—Reg, Integ and Comp Phgy, Oct. 7, 2004, 288:R623-R629, New York, NY.
Bassett et al: "Generation of Electric Potentials by Bone in Response to Mechanical Stress," Science Magazine, 137, pp. 1063-64 (1962).
PCT International Search Report dated Aug. 30, 2007 for PCT/US2007/005793 (Aug. 30, 2007).
PCT notification of transmittal of the ISR and Written Opinion of ISA for PCT/US2007/005794 (Aug. 30, 2007).
PCT notification of transmittal of the ISR and Written Opinion of ISA for PCT/US2007/005792 (Sep. 12, 2007).
PCT International Search Report (ISR) for PCT/US2007/015732 (Jan. 24, 2008).
Goodard at al.: "Reversal of Lower-limb Edema by Calf Muscle Pump Stimulation,". J. Cardiopulmonary Rehab. & Prevention, 28:174-179 (May/Jun. 2008).
Walsh, W.R, at al,: "Influence of Dynamic Motion Therapy on bone ingrowth into a bone graft substitute", Surg. & Ortho. Res, Labs., Univ. of New S. Wales, w.walsh@unsw.edu.au.

* cited by examiner

SYSTEM AND METHOD FOR A LOW PROFILE VIBRATING PLATE

PRIORITY

This patent application claims priority to a provisional application filed on Jul. 11, 2006 and assigned U.S. Provisional Application Ser. No. 60/830,286; the entire contents of which are incorporated herein by reference.

BACKGROUND

1. Technical Field

The present disclosure relates generally to non-invasive medical treatment procedures. In particular, the present disclosure relates to a method and system for treating body ailments or tissue conditions such as vascular disease, deep vein thrombosis, orthostatic intolerance, reduced blood flow, weak bone structure, orthostatic hypotension, or other conditions.

2. Background

Medical treatments for body ailments or tissue conditions that contact the outer surface of the body rarely, if ever, attain the maximum benefit possible. The condition of the patient may diminish the effectiveness of the medical treatment or make the entire treatment ineffective. For example, although compression devices can be applied to the surface of the body to reduce the incidence of a tissue condition such as deep vein thrombosis (DVT) in some patients, conditions such as swelling (edema), or obesity may diminish the effectiveness of the compression device and/or make the entire treatment ineffective. Moreover, adverse events during the treatment such as skin irritation, or pressure ulcer may be problematic and decrease the effectiveness of the treatment resulting in the need to discontinue or change the treatment and/or device to obtain a desired beneficial effect, or in some cases continue treatment subjecting the patient to prolonged discomfort.

Accordingly, there remains room for improvement in tissue treatment regimens for body ailments or tissue conditions. What are needed are new tissue treatment apparatuses and methods for treating body ailments and/or tissue conditions.

SUMMARY

The present disclosure provides a low profile vibrating plate system for providing a medical treatment of body ailments or tissue conditions such as vascular disease, deep vein thrombosis, orthostatic intolerance, reduced blood flow, weak bone structure, orthostatic hypotension, or other conditions. The disclosed system includes a low profile base having a cavity, a platform having an upper portion and a lower portion, the platform in juxtaposed alignment with the low profile base. The platform is free moving within the cavity. The platform's upper portion provides a rigid base upon which a patient is to contact.

The apparatus in accordance with the present disclosure further includes a first magnetic layer positioned adjacent to the platform, the first magnetic layer configured for imparting periodic vibrations at a predetermined frequency to the platform. In some embodiments, a second magnetic layer is affixed to the lower surface of the cavity, and is aligned with the first magnetic layer for at least a portion of time and for at least a portion of time has polarity equal to the polarity of the first magnetic layer which results in repulsion of the first and second magnetic layers from one another. A controller in electrical communication with the second magnetic layer is configured for control of the polarity and magnetic field intensity of the second magnetic layer.

The first and second magnetic layers can be made of materials such as ferromagnetic objects, electromagnets, flexible magnets, injection molded magnets, neodymium iron boron magnets, samarium cobalt magnets, alnico magnets, ceramic magnets, or combinations thereof.

In some embodiments, the device is configured so the platform vibrates vertically and/or horizontally with a frequency of between 0 Hz and 10 KHz such as 30 Hz. Furthermore, in some embodiments, the platform vibrates vertically and/or horizontally for a distance of about 1 micrometer to about 40 micrometers. Stops may limit the distance to a predetermined displacement range.

In some embodiments, the device in accordance with the present disclosure is configured to have one or more elastic layers within the cavity of the low profile base. The elastic layers may be positioned between the first and second magnetic layers, and/or between the magnetic layers and the platform.

In some embodiments, the device in accordance with the present disclosure includes a third magnetic layer disposed upon the platform. Optionally, a fourth magnetic layer may be disposed upon the low profile base. In some embodiments, the third magnetic layer is configured to generate a static magnetic field and the fourth magnetic layer is configured to generate a dynamic magnetic field, having any combination of alternating polarities and varying magnetic field intensities.

Additionally, the present disclosure provides a method for using a low profile vibrating plate as a medical treatment of ailments or tissue conditions such as vascular disease, deep vein thrombosis, orthostatic intolerance, reduced blood flow, weak bone structure, orthostatic hypotension, or other conditions. The disclosed method provides a low profile base having a cavity and a platform dimensioned to fit within the cavity in a free moving manner. The platform provides a lower portion and an upper portion, wherein the upper portion provides a rigid base upon which a patient is to contact.

The disclosed method, additionally, provides for generating a first magnetic field using a first magnetic layer configured for generating a static magnetic field affixed to the platform's lower portion and a second magnetic layer configured for generating a dynamic magnetic field affixed to a lower surface of the cavity. The second magnetic layer is aligned with the first magnetic layer for at least a portion of time and for at least a portion of time has a polarity equal to the polarity of the first magnetic layer. The method further performs the step of controlling the dynamic magnetic field by adjustment of polarity and magnetic field intensity of the second magnetic layer.

The use of magnetic field generating devices in the embodiments of the present disclosure provides several key benefits. Magnetic field generating devices allow for a more compact form-factor for the vibrating plate, which allows for increased portability. Additionally, the devices can be set upon or within surfaces to facilitate use thereof.

In yet another embodiment, the present disclosure relates to a wearable apparatus for treating tissue ailments including a low profile base, a platform in juxtaposed alignment with the low profile base, the platform having an upper portion and a lower portion; and a first magnetic layer positioned adjacent to the platform, the first magnetic layer configured for imparting periodic vibrations at a predetermined frequency to the platform. The apparatus may be shaped to fit within a shoe or sandal. Furthermore, the apparatus may be incorporated into the body of a shoe or sandal. The apparatus may also include a vamp having a first end and a second end, both ends of the vamp being adjustably disposed within a track on the body of the apparatus. Accordingly, the vamp may be adjustable along the length of the apparatus.

In some embodiments, the upper portion of the platform is textured. Moreover, the apparatus may be disposed within the insole of a shoe. It is envisioned that the wearable apparatus may also include a second magnetic layer disposed upon the base, the second magnetic layer being aligned with the first magnetic layer, wherein the polarity of the first magnetic layer is substantially equal to the polarity of the second magnetic layer such that the first magnetic layer and the second magnetic layer repel one another. Accordingly, the platform can vibrate vertically and/or horizontally at a frequency of between 0 Hz and 10 KHz. Moreover, the platform can vibrate vertically and/or horizontally a distance of about 1 micrometer to about 40 micrometers.

In some wearable embodiments, a first elastic layer may be positioned between the first magnetic layer and the platform, and a second elastic layer may be positioned between the second magnetic layer and the first magnetic layer. A third magnetic layer may be disposed upon the platform, and a fourth magnetic layer may be disposed upon the low profile base.

BRIEF DESCRIPTION OF THE DRAWINGS

These and other features, aspects, and advantages of the present disclosure will become better understood with regard to the following description, appended claims, and accompanying drawings wherein:

DESCRIPTION OF THE PREFERRED EMBODIMENTS

The present disclosure provides for the use of vibrational treatment in treating and preventing body ailments or tissue conditions. For example, apparatus and methods in accordance with the present disclosure are for therapeutically treating body ailments or tissue conditions such as vascular disease, deep vein thrombosis, orthostatic intolerance, reduced blood flow, weak bone structure, orthostatic hypotension, or other conditions. Furthermore, apparatus and methods in accordance with the present disclosure provide an oscillating platform apparatus that is highly stable, and substantially insensitive to the position of the patient thereon, while providing low displacement, high frequency mechanical loading of tissue sufficient to reduce, reverse, or prevent body ailments, tissue conditions, or other conditions. Moreover, the low profile device is suitable to be attached or set within surfaces such as flooring so that the benefits can be obtained by users during every day activities.

Figure 1:
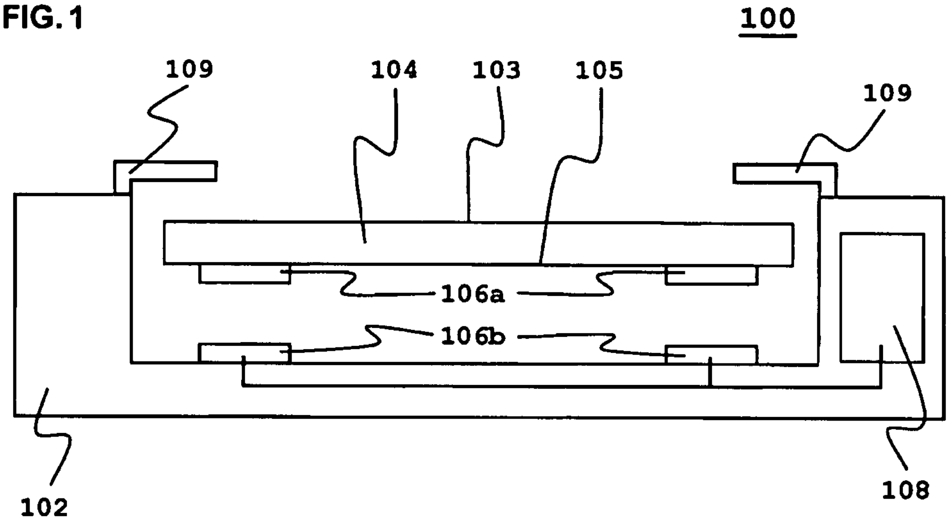
FIG. 1 is a schematic view of an embodiment of a low profile vibrating plate in accordance with the present disclosure.

Referring to FIG. 1, an embodiment of the present disclosure provides a low profile vibrating plate system 100 for use in medial treatments. The system 100 includes a low profile base or actuator plate 102 and a platform 104 having an upper portion 103 and a lower portion 105. The platform 104 rests within a cavity formed on the top surface of the low profile base 102. Two magnetic layers **106*a* and 106*b* are positioned, first magnetic layer 106*a*, on the underside of the platform 104 and, a second magnetic layer 106*b*, on the lower surface of the cavity, such that the first magnetic layer 106*a* on the platform 104 and the second magnetic layer 106*b* on the low platform base 102 are paired. Each paired magnet layer 106*a* and 106*b* are set with equivalent polarities facing each other, thus providing a repellant force between the pair and consequently, causing the platform 104 to levitate above the low profile base 102. The second magnetic layer 106*b* has adjustable magnetic properties (e.g., polarity, magnetic field intensity) controlled by a processor 108 in electrical communication with the second magnetic layer 106*b***. It is envisioned that the processor can be in communication with either the first, second, or both magnetic layers.

In embodiments, the first magnetic layer **106*a* on the platform 104 include static magnetic field generating devices, such as permanent Ferro-magnets, but may also be electromagnets, coils, or dynamic magnetic field generating devices. In embodiments, the first magnetic layer is made of any suitable magnetic material such as one or more static ferromagnetic objects, electromagnets, flexible magnets, injection molded magnets, neodymium iron boron magnets, samarium cobalt magnets, alnico magnets, ceramic magnets, or combinations thereof. In one particular embodiment, first magnetic layer 106*a* is a flexible magnet configured to cover the underside of the platform 104. In embodiments, the first magnetic layer 106*a*** can have a thickness of about 1 mm to about 5 cm.

The second magnetic layer 106*b*, can be a set of electromagnets, coils, or other dynamic magnetic field generating devices. In embodiments, the second magnetic layer 106*b*, can be one or more static ferromagnetic objects, electromagnets, flexible magnets, injection molded magnets, neodymium iron boron magnets, samarium cobalt magnets, alnico magnets, ceramic magnets, or combinations thereof. In one particular embodiment, second magnetic layer 106*b* is a flexible magnet configured to coat and/or cover the low platform base 102. In embodiments, the second magnetic layer can have a thickness of about 1 mm to about 5 cm.

By varying the field intensity and/or alternating the polarity of the second magnetic layer 106*b* to create a dynamic magnetic field, a vertical vibration of the platform 104 can be induced. The vibrational frequency is determined by the rate of change of the magnetic properties, while the amplitude of the vibration is determined by the magnetic field intensity. Additionally, the magnetic field intensity may be increased or decreased as needed, depending on a patient's weight, to properly position and vibrate the platform 104.

In embodiments, the field intensity and/or alternating of the polarity of the second magnetic layer 106*b* is configured for imparting periodic vibrations at a predetermined frequency to the platform 104. Accordingly, in embodiments, the platform 104 vibrates vertically with a frequency of between 0 Hz and 10 KHz. In particular embodiments, the platform 104 vibrates vertically with a frequency of about 30 KHz. In embodiments, the platform vibrates vertically a distance of about 1 micrometer to about 40 micrometers.

In embodiments, the field intensity and/or alternating of the polarity of the second magnetic layer 106*b* can be controlled by sending a signal to processor 108 in electrical communication with the second magnetic layer 106*b*. The signal can be sent manually and/or remotely by signaling with infrared, radiofrequency, or any other signal available in the electromagnetic spectrum.

To limit travel of the platform 104, one or more stops 109 may be affixed to the low profile base 102 at the upper limit of the platform's 104 travel, thus preventing the platform 104 from separating from the low profile base 102. The stops 109 may be bumpers in this case, or alternatively, the stops may be a cable, spring or elastic band connected to the underside of the platform 104 and the bottom of the cavity of the low profile base 102.

Figure 2:
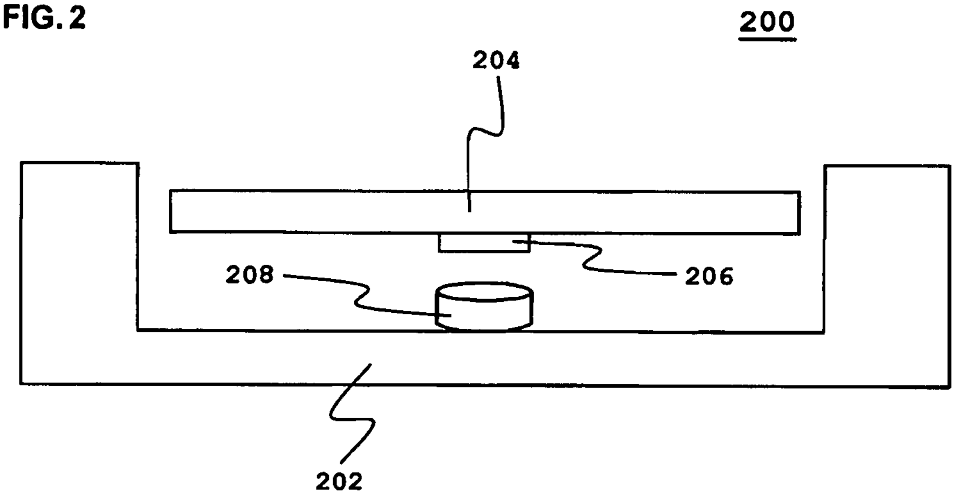
FIG. 2 is a schematic view of an alternate embodiment of a low profile vibrating plate in accordance with the present disclosure.

Referring to FIG. 2, an alternate embodiment of the present disclosure is illustrated. The system 200 has a supporting low profile base or actuator plate 202 with a central cavity and a platform 204, which fits within the cavity. A first magnetic layer 206, suitable for generating a magnetic field, is affixed and positioned centrally on the underside of the platform 204. In embodiments, the magnetic layer 206 is capable of generating a magnetic field and is a permanent Ferro-magnetic device, and/or made of any suitable magnetic material such as one or more static or dynamic ferromagnetic objects, electromagnets, flexible magnets, injection molded magnets, neodymium iron boron magnets, samarium cobalt magnets, alnico magnets, ceramic magnets, or combinations thereof.

Aligned directly below the first magnetic layer 206 is a second magnetic layer 208 configured to generate a magnetic field, which is controllable as described above for the embodiment in FIG. 1. In embodiments, the second magnetic layer 208 is capable of generating a magnetic field and is a permanent Ferro-magnetic device, and/or made of any suitable magnetic material such as one or more static or dynamic ferromagnetic objects, electromagnets, flexible magnets, injection molded magnets, neodymium iron boron magnets, samarium cobalt magnets, alnico magnets, ceramic magnets, or combinations thereof.

Figure 3:
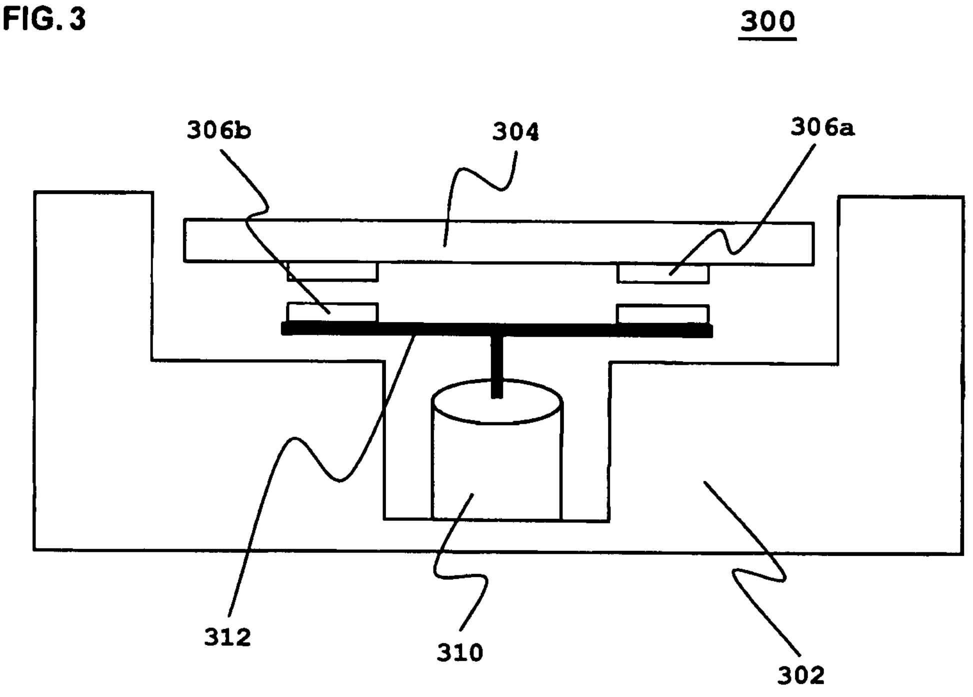
FIG. 3 is a schematic view of another alternate embodiment of a low profile vibrating plate in accordance with the present disclosure.

Referring to FIG. 3, yet another embodiment of the present disclosure is illustrated. The system 300 imparts vibrational motion to the platform 304 via a varying magnetic field produced by a magnetic layer 306*b* positioned on either end of a horizontal arm 312 attached to a motor 310. The motor 310 is located within a central cavity of the low profile base 302.

As the horizontal arm 312 rotates, the magnets 306*b* align and unalign periodically with magnetic layers 306*a* attached to the underside of the platform 304. The magnetic layers 306*a* and 306*b* are configured to provide repulsive force against each other, so that, upon alignment of the magnetic layers 306*a* and 306*b*, the platform 304 is levitated upward and upon unalignment, the repulsive force is removed allowing the platform 304 to drop downward. The speed at which the motor 310 rotates the magnetic layers 306*b* directly determines the vibrational frequency of the plate, thus by varying the rotational speed of the motor 310, the frequency is adjusted to provide optimal therapeutic benefit to the patient. In embodiments, the magnetic layer 306*a* and 306*b* are capable of generating a magnetic field and can be a permanent Ferro-magnetic device, and/or made of any suitable magnetic material such as one or more static or dynamic ferromagnetic objects, electromagnets, flexible magnets, injection molded magnets, neodymium iron boron magnets, samarium cobalt magnets, alnico magnets, ceramic magnets, or combinations thereof.

Figure 4:
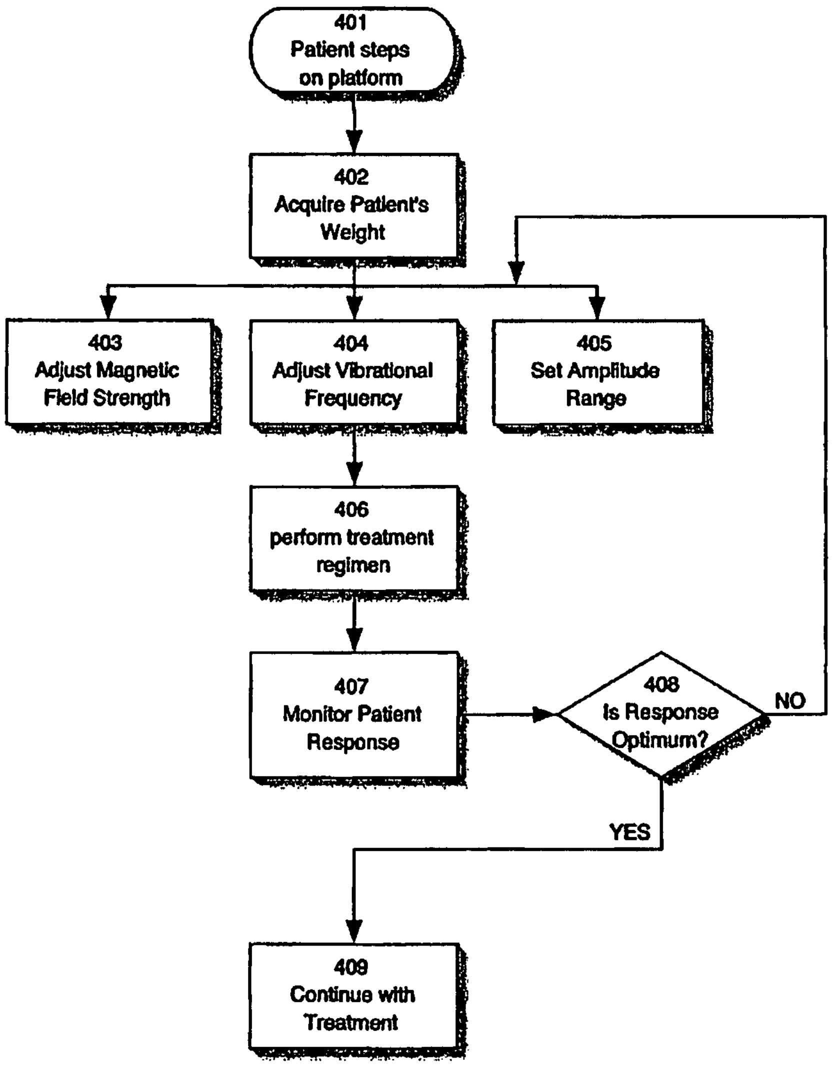
FIG. 4 is a flowchart of the steps performed by an embodiment of a low profile vibrating plate in accordance with the present disclosure.

The flowchart of FIG. 4 illustrates the steps performed by an embodiment of the present disclosure. Beginning with step 401, a patient is positioned on the platform 102. In step 402, the patient's weight is measured and relayed to the controller 108. Any of several well-known methods for measuring weight may be incorporated within the system 100. Alternatively, the weight may be measured prior to step 401 and the value entered into the controller manually by the system operator. In Step 403, the weight measurement is used for determining the proper magnetic field strength by the controller 108. The treatment parameters are set in step 404, where the desired vibrational frequency is relayed to the controller 108, and 405, where the amplitude of the vibration treatment is entered. The treatment regimen is administered in step 406 and patient response is monitored and in step 407. The monitor responses are further evaluated in step 408. If the patient is responding appropriately to the treatment, then the treatment continues in step 409 for the duration of the treatment session. However, if the patient is experiencing difficulties or other inappropriate responses are detected, then the treatment session is stopped and the treatment parameters are adjusted in steps 404 and 405. After readjusting the parameters, a new round of treatment is initiated, as previously described, continuing on from step 406.

Figure 5:
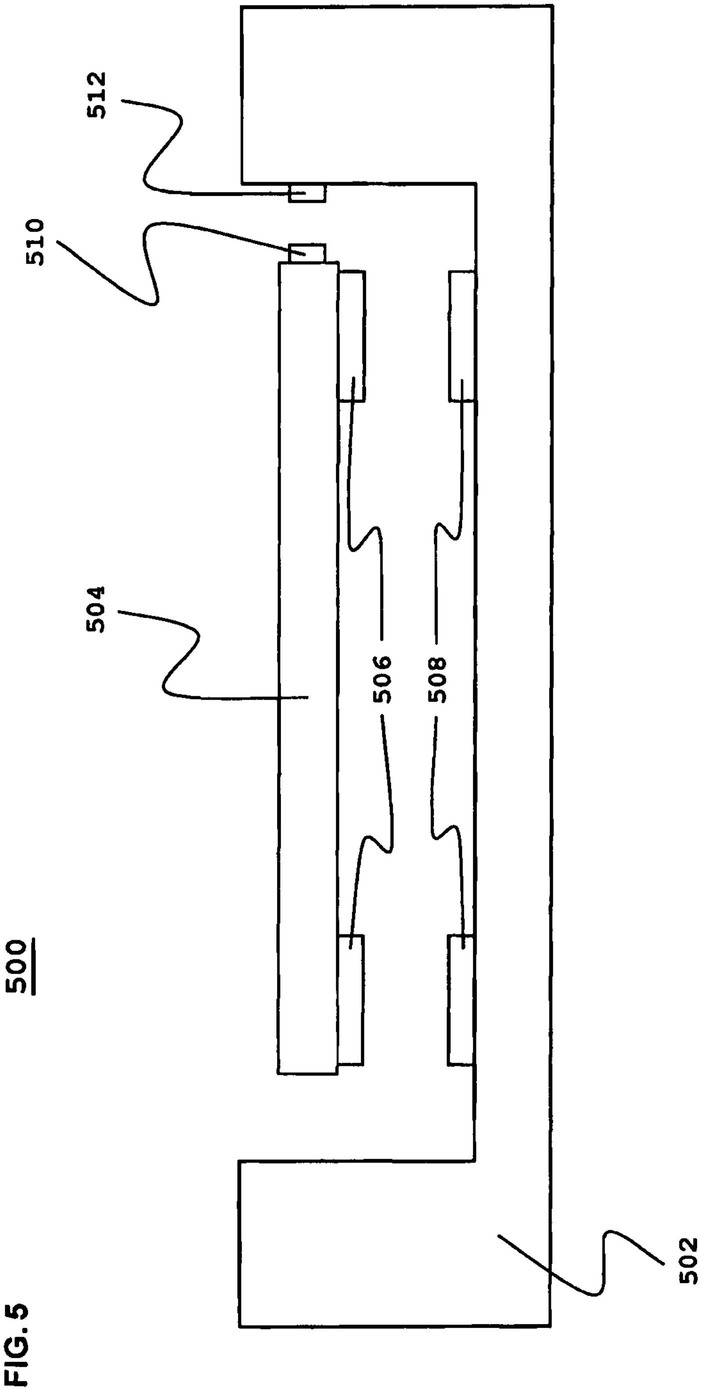
FIG. 5 is a schematic view of another alternate embodiment of a low profile vibrating plate in accordance with the present disclosure.

Referring to FIG. 5, yet another embodiment of the present disclosure is illustrated. As in the embodiment of FIG. 1, the system 500 has a supporting low profile base 502 with a central cavity and a platform 504, which fits within the cavity. A first magnetic layer 506 configured to generate a magnetic field is affixed and positioned on the underside of the platform 504. The first magnetic layer 506 can be made of permanent Ferro-magnetic materials and/or made of any suitable magnetic material such as one or more static or dynamic ferromagnetic objects, electromagnets, flexible magnets, injection molded magnets, neodymium iron boron magnets, samarium cobalt magnets, alnico magnets, ceramic magnets, or combinations thereof.

Aligned directly below the first magnetic layer 506 is a second magnetic layer 508 configured for generating a magnetic field, which is controllable as described above for the embodiment in FIG. 1. The second magnetic layer 508 may be made of permanent Ferro-magnetic materials and/or made of any suitable magnetic material such as one or more static or dynamic ferromagnetic objects, electromagnets, flexible magnets, injection molded magnets, neodymium iron boron magnets, samarium cobalt magnets, alnico magnets, ceramic magnets, or combinations thereof.

Additionally, a third magnetic layer 510 configured for generating a magnetic field is positioned along at least one side of the platform 504. As with the first magnetic layer 506, the third magnetic layer 510 can be made from permanent Ferro-magnetic materials and/or any suitable magnetic material such as one or more static or dynamic ferromagnetic objects, electromagnets, flexible magnets, injection molded magnets, neodymium iron boron magnets, samarium cobalt magnets, alnico magnets, ceramic magnets, or combinations thereof.

A fourth magnetic layer configured for generating a magnetic field 512 is located and aligned opposite the third magnetic layer 510 on a side wall of the cavity of the low profile base 502. The fourth magnetic layer 512 is controllable in the same manner as described for the second magnetic layer 508, such that a controlled horizontal vibration is imparted on the platform 504. By alternating the magnetic polarity of the fourth magnetic layer 512, a horizontal vibration of the platform 504 is induced. Additional magnet layers may be placed on a perpendicular side of the platform 504 and cavity wall to induce a third dimension of vibration of the platform 504.

In embodiments, the field intensity and/or alternating of the polarity of the fourth magnetic layer 512 is configured for imparting periodic vibrations at a predetermined frequency to the platform 504. Accordingly, in embodiments, the platform 504 vibrates horizontally with a frequency of between 0 Hz and 10 KHz. In particular embodiments, the platform 504 vibrates horizontally with a frequency of about 30 Hz.

Figure 6:
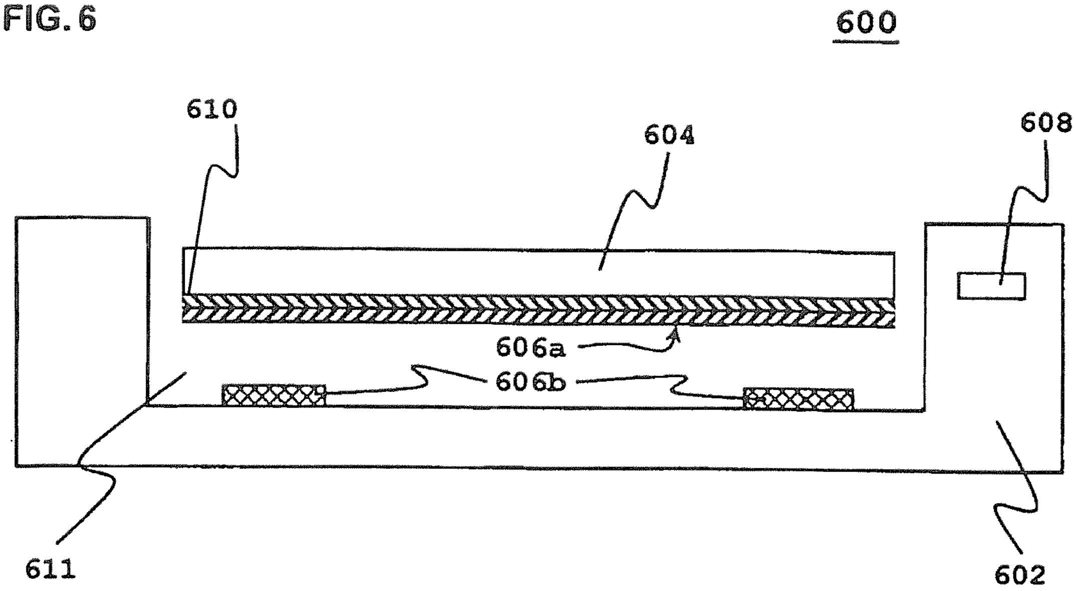
FIG. 6 is a schematic view of another alternate embodiment of a low profile vibrating plate in accordance with the present disclosure.

Referring to FIG. 6, yet another embodiment of the present disclosure is illustrated. The system 600 includes a low profile base 602 and a platform 604. The platform 604 rests on top of a first elastic layer 610 within a cavity 611 formed on the top surface of the low profile base 602. Two magnetic layers 606*a* and 606*b* are positioned, first magnetic layer 606*a*, on the underside of the first elastic layer 610 and, a second magnetic layer 606*b*, on the top surface of the low profile base 602, such that the first magnetic layer 606*a* and the second magnetic layer 606*b* on the low platform base 102 are paired. Each paired magnet layer 606*a* and 606*b* are set with equivalent polarities facing each other, thus providing a repellant force between the pair and consequently, causing the platform 604 to levitate above the first elastic layer 610. The second magnetic layer 606*b* has adjustable magnetic properties (e.g., polarity, magnetic field intensity) controlled by a processor 608 in electrical communication with the second magnetic layer 606*b*.

In embodiments, the first magnetic layer 606*a* below first elastic layer 610 includes static magnetic field generating devices, such as permanent Ferro-magnets, but may also include electromagnets, coils, or dynamic magnetic field generating devices. In embodiments, the first magnetic layer 606*a* is made of any suitable magnetic material such as one or more static ferromagnetic objects, electromagnets, flexible magnets, injection molded magnets, neodymium iron boron magnets, samarium cobalt magnets, alnico magnets, ceramic magnets, or combinations thereof. In one particular embodiment, first magnetic layer 606*a* is a flexible magnet configured to cover the underside of the first elastic layer 610. In embodiments, the first magnetic layer 606*a* can have a thickness of about 1 mm to about 5 cm.

The second magnetic layer 606*b*, can be a set of electromagnets, coils, or other dynamic magnetic field generating devices. In embodiments, the second magnetic layer 606*b*, can be one or more static ferromagnetic objects, electromagnets, flexible magnets, injection molded magnets, neodymium iron boron magnets, samarium cobalt magnets, alnico magnets, ceramic magnets, or combinations thereof. In one particular embodiment, second magnetic layer 606*b* is a flexible magnet configured to coat or cover the low platform base 602. In embodiments, the second magnetic layer can have a thickness of about 1 mm to about 5 cm.

By varying the field intensity and/or alternating the polarity of the second magnetic layer 606*b* a vertical vibration of the platform 604 can be induced. The vibrational frequency is determined by the rate of change of the magnetic properties, while the amplitude of the vibration is determined by the magnetic field intensity. Additionally, the magnetic field intensity may be increased or decreased as needed, depending on a patient's weight, to properly position and vibrate the platform 604. In embodiments, plat form 604 vibrates vertically with a frequency of between 0 Hz and 10 KHz.

First elastic layer 610 is configured to create support and fit within system 600. The first elastic layer 610 can be any elastomeric material such as rubber, cloth/rubber combinations, or soft elastic material, such as foamed polyurethane (PU). The first elastic layer 610 may have a suitable density, so that it is readily deformed when being squeezed and able to recover quickly and freely from squeezing. The main body of the first elastic layer 610 may have an overall height or size properly decided depending on a use intended for it. For example, it may be 1 mm to 5 cm in height for suitably positioning in system 600.

Figure 7:
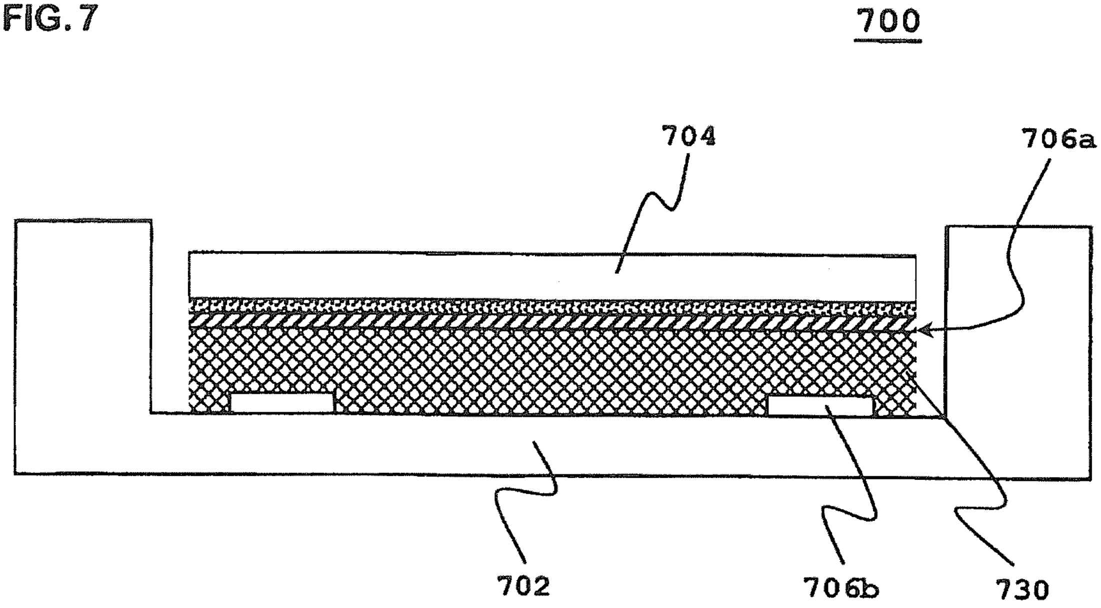
FIG. 7 is a schematic view of another alternate embodiment of a low profile vibrating plate in accordance with the present disclosure.

Referring to FIG. 7, yet another embodiment of the present disclosure is illustrated. The system 700 imparts vibrational motion to the platform 704 via a varying magnetic field produced by a magnetic layer 706*b* positioned on the low profile base or actuator plate 702. The magnetic layers 706*a* and 706*b* are configured to provide repulsive force against each other while being separated by a second elastic layer 730.

Second elastic layer 730 is configured to create support and fit within system 700. The second elastic layer 730 can be any elastomeric material such as rubber, cloth/rubber combinations, or soft elastic material, such as foamed polyurethane (PU). The second elastic layer 730 may have a suitable density, so that it is readily deformed when being squeezed and able to recover quickly and freely from squeezing. The main body of the second elastic layer may have an overall height or size properly decided depending on a use intended for it. For example, it may be 1 mm to 5 cm in height for suitably positioning in system 700.

Figure 8:
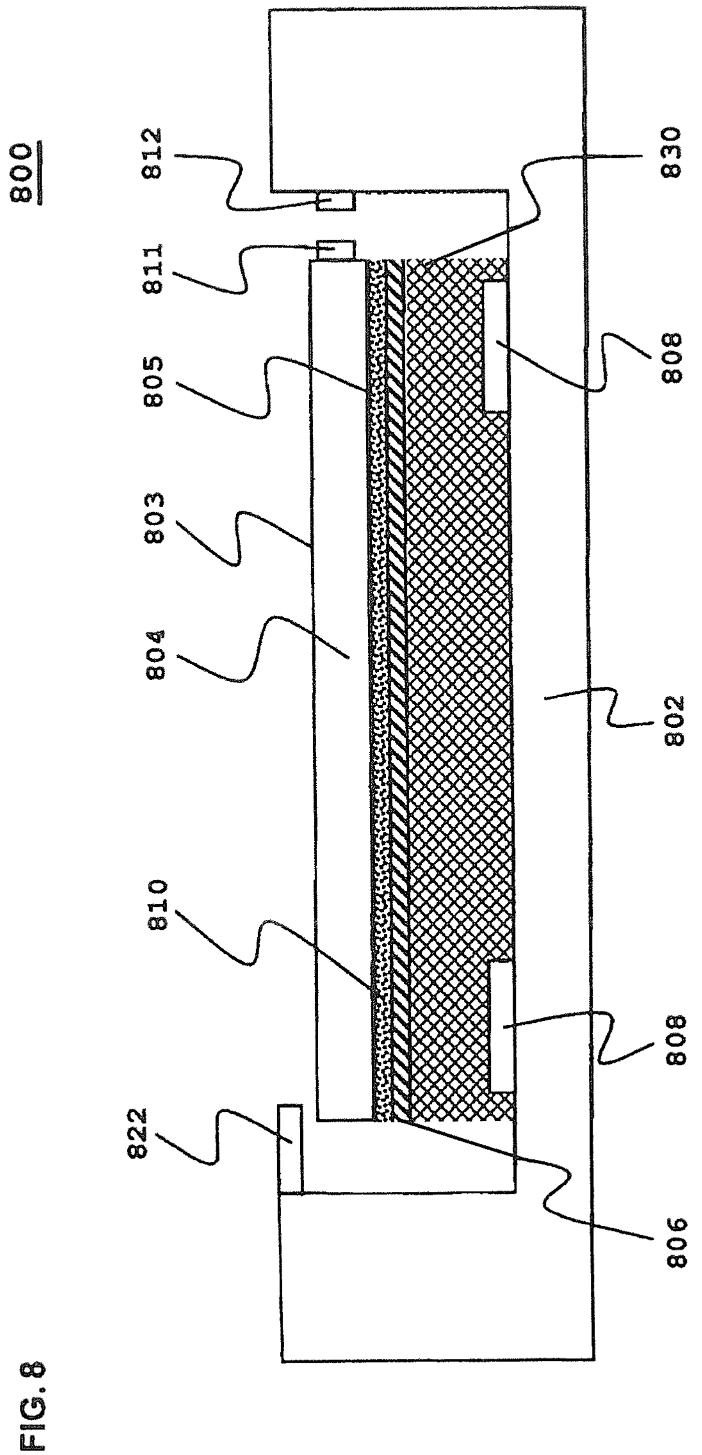
FIG. 8 is a schematic view of another alternate embodiment of a low profile vibrating plate in accordance with the present disclosure.

Referring to FIG. 8, yet another embodiment of the present disclosure is illustrated. The system 800 has a supporting low profile base 802 with a central cavity and a platform 804, which fits within the cavity. A first elastic layer 810 is positioned below platform 804 having an upper portion 803 and a lower portion 805 within the cavity. A first magnetic layer 806 configured to generate a magnetic field is positioned on the underside of the first elastic layer 810. The first magnetic layer 806 can be made of permanent Ferro-magnetic materials and/or made of any suitable magnetic material such as one or more static ferromagnetic objects, electromagnets, flexible magnets, injection molded magnets, neodymium iron boron magnets, samarium cobalt magnets, alnico magnets, ceramic magnets, or combinations thereof.

Aligned directly below the first magnetic layer 806 is a second elastic layer 830. Second elastic layer 830 is configured to create support and fit within system 800. The second elastic layer 830 can be any elastomeric material such as rubber, cloth/rubber combinations, or soft elastic material, such as foamed polyurethane (PU). The second elastic layer 830 may have a suitable density, so that it is readily deformed when being squeezed and able to recover quickly and freely from squeezing. The main body of the second elastic layer may have an overall height or size properly decided depending on a use intended for it. For example, it may be 1 mm to 5 cm in height for suitably positioning in system 800.

Positioned adjacent to the second elastic layer 830 is second magnetic layer 808 configured for generating a magnetic field, which is controllable as described above for the embodiment in FIG. 1. The second magnetic layer 808 may be made of permanent Ferro-magnetic materials and/or made of any suitable magnetic material such as one or more static or dynamic ferromagnetic objects, electromagnets, flexible magnets, injection molded magnets, neodymium iron boron magnets, samarium cobalt magnets, alnico magnets, ceramic magnets, or combinations thereof.

Additionally, a third magnetic layer 811 configured for generating a magnetic field is positioned along at least one side of the platform 804. As with the first magnetic layer 806, the third magnetic layer 810 can be made from permanent Ferro-magnetic materials and/or any suitable magnetic material such as one or more static or dynamic ferromagnetic objects, electromagnets, flexible magnets, injection molded magnets, neodymium iron boron magnets, samarium cobalt magnets, alnico magnets, ceramic magnets, or combinations thereof.

A fourth magnetic layer configured for generating a magnetic field 812 is located and aligned opposite the third magnetic layer 811 on a side wall of the cavity of the low profile base 802. The fourth magnetic layer 812 is controllable in the same manner as described for the second magnetic layer 808, such that a controlled horizontal vibration is imparted on the platform 804. By alternating the magnetic polarity of the fourth magnetic layer 812, a horizontal vibration of the platform 804 is induced. Additional magnet sets may be placed on a perpendicular side of the platform 804 and cavity wall to induce a third dimension of vibration of the platform 804. Moreover, stops 822 can be added to platform 802 to limit the movement of platform 804.

In embodiments, the field intensity and/or alternating of the polarity of the fourth magnetic layer 812 is configured for imparting periodic vibrations at a predetermined frequency to the platform 804. Accordingly, in embodiments, the platform 804 vibrates horizontally with a frequency of between 0 Hz and 10 KHz. In particular embodiments, the platform 804 vibrates horizontally with a frequency of about 30 Hz.

Body ailments or tissue conditions such as vascular diseases or disorders are alleviated, prevented and/or treated in accordance with the present disclosure by the application of one or more vibrating plates to the surface of the patient's body. The vibrating mechanism can be applied to skin adjacent to the body ailment for duration sufficient to reduce or eliminate undesirable ailments or conditions. As used herein the word "treat," "treating" or "treatment" refers to using the apparatus of the present disclosure prophylactically to prevent outbreaks of one or more undesirable ailments and/or tissue conditions, or therapeutically to ameliorate an existing ailment and/or tissue condition. A number of different treatments are now possible, which reduce and/or eliminate ailments or conditions such as vascular disease, deep vein thrombosis, orthostatic intolerance, reduced blood flow, weak bone structure, orthostatic hypotension, other tissue conditions, or combinations thereof.

As used herein "ailment" refers to any body disorder or tissue condition such as circulatory disease, vascular disease including peripheral vascular disease, cardiac disease and/or orthostatic intolerance. A used herein "vascular disease" refers to any disease of the blood vessels. As used herein "peripheral vascular disease" refers to diseases of blood vessels outside the heart and brain, including but not limited to, narrowing of vessels that carry blood to leg and arm muscles, and/or which may cause pain in exercising or walking. As used herein "orthostatic intolerance" refers to the symptoms during upright standing relieved by recumbency, as well as illnesses that contribute thereto.

Non-limiting examples of vascular disorders include acrocyanosis, arteriovenous fistula, blood clots in the veins, blood clotting disorders, Buerger's Disease, central venous insufficiency, chronic venous insufficiency, deep vein thrombosis (DVT), erythromelalgia, gangrene, ischemia such as to the fingers, hands, toes, and feet, Klippel-Trenaunay Syndrome, lymphedema, lipedema, peripheral vascular/arterial disease, thrombophlebitis/phlebitis, peripheral artery disease, peripheral venous disease, phlebitis and thrombosis, Raynaud's Disease/phenomenon, varicose and spider veins, vasculitis, venostasis, and combinations thereof.

Non-limiting examples of cardiac disease include angioneurotic edema, behcet syndrome, cardiac tamponade, cardiomegaly, cardimyopathy (dilated, hypertrophic, restrictive), cardiovascular disease, cartoid stenosis, Churg Strauss Syndrome, Ebstein's anomaly, Eisenmenger Complex, embolism (cholesterol), endocarditis, fibromuscular dysplasia, heart diseases, hematoma, Hippel-Lindau Disease, hyperemia, hypertension, hypotension, intermittent claudication, intracranial aneurysm, Klippel-Trenaunay-Weber Syndrome, long XT syndrome, microvascular angina, moyamoya disease, mucocutaneous lymph node syndrome, phlebitis, polyarteritis nodosa, pulmonary atresia, Raynaud disease, Sneddon Syndrome, Takayasu's Arteritis, telangiectasia (hereditary hemorrhagic), telangiectassis, temporal arteritis, thromboangitis obliterans, thrombophlebitis, thrombosis, vasculitis, vasospasm, Williams Syndrome, Wolff-Parkinson-White Syndrome, and combinations thereof.

Non-limiting examples of illnesses that contribute to orthostatic intolerance include disorders of blood flow, heart rate and blood pressure regulation that are present in any position of the patient.

Other ailments or conditions such as fibromyalgia are suitable for treatment in accordance with the present disclosure.

In embodiments, the apparatus for use in accordance with the present disclosure provides vibrations in an effective amount to improve an ailment and/or condition. As used herein "effective amount" refers to an amount of vibration in accordance with the present disclosure that is sufficient to induce a particular positive benefit to a patient having an ailment. The positive benefit can be health-related, or it may be more cosmetic in nature, or it may be a combination of the two. In embodiments, the positive benefit is achieved by contacting the patient's body with vibrations to improve one or more ailments or tissue conditions. In embodiments, the positive benefit is achieved by contacting skin with one or more vibrating plates to alleviate symptoms caused by vascular disease, deep vein thrombosis, orthostatic intolerance, reduced blood flow, weak bone structure, orthostatic hypotension, other conditions, and combinations thereof. In embodiments, the positive benefit is achieved by applying vibrations and magnetic field to cure an ailment or tissue condition.

The particular magnetic field, and the vibration frequency employed, generally depends on the purpose for which the treatment is to be applied. For example, the duration and vibration frequency of application can vary depending upon the type and severity of the ailment.

Figure 9:
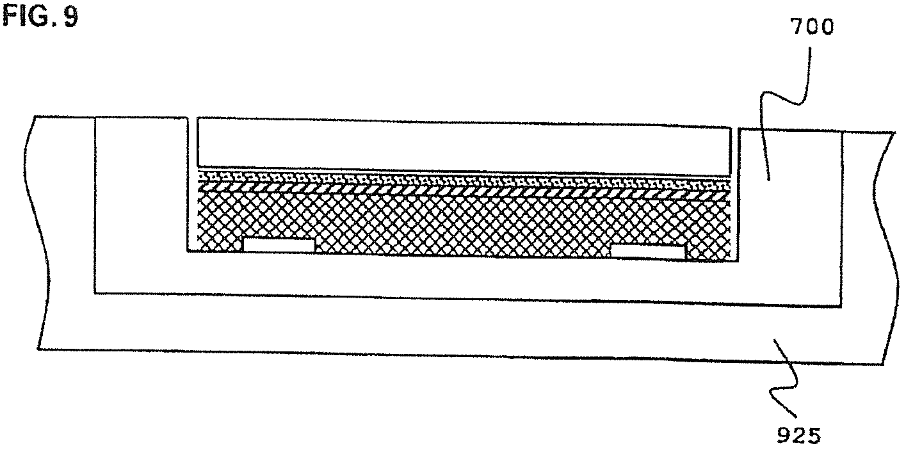
FIG. 9 is a schematic view of the low profile vibrating plate in accordance with FIG. 7 set within a surface.

In order to facilitate use of the device for providing vibrational energy while performing every day tasks, the device can be incorporated into various fixed positions. For example, the low profile base can be placed into various objects such as shoes, socks, sandals and the like. Moreover, the low profile base can be positioned upon or within flooring such as the floor of a car, bus, train, plane and the like. Referring to FIG. 9, a system 700 in accordance with the present disclosure is shown submerged within a substrate 925. Accordingly, a person sitting above system 700 can receive the benefits of the apparatus and methods in accordance with the present invention while performing every day task. Substrate 925 may be the floor of a car, insole of a shoe or sandal, or any substrate where one would place one's foot or feet.

Figure 10A:
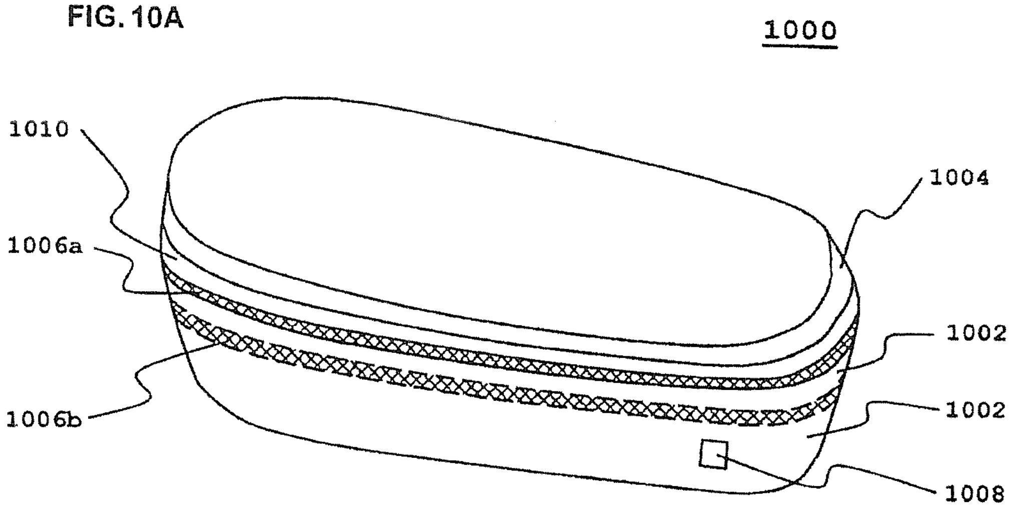
FIG. 10A is a schematic view of another alternate embodiment of a low profile vibrating plate in accordance with the present disclosure.

Referring now to FIG. 10A, yet another embodiment of the present disclosure is illustrated. The system 1000 includes a low profile base 1002 and a platform 1004 sized and shaped to match the foot or feet of a user. In order to facilitate use thereof, apparatus 1000 is wearable and sized for inserting into one or more socks, shoes, boots, or the like. As used herein "wearable" refers to a device which is easily or conveniently transported and/or worn by the user. Accordingly, the device can also be built directly into the structure of one or more socks, shoes, boots, or similar devices. Here, the platform 1004 is configured for placement upon or connection with the insole or the exterior bottom of a shoe or sandal like device located directly beneath the foot. The platform 1004 may be removable and replaceable. Furthermore the platform can be configured with pads or contours to provide comfort and support to the foot of the user. The platform 1004 rests on top of a first elastic layer 1010 disposed upon the low profile base 1002. Two magnetic layers 1006*a* and 1006*b* are positioned, first magnetic layer 1006*a*, on the underside of the first elastic layer 1010 and, a second magnetic layer 1006*b*, within the low profile base 1002, such that the first magnetic layer 1006*a* and the second magnetic layer 1006*b* within the low profile base 1002 are paired. Each paired magnet layer 1006*a* and 1006*b* are set with equivalent polarities facing each other, thus providing a repellant force between the pair and consequently, causing the platform 1004 to levitate above the first elastic layer 1010. The second magnetic layer 1006*b* has adjustable magnetic properties (e.g., polarity, magnetic field intensity) controlled by a processor 1008 in electrical communication with the second magnetic layer 1006*b*.

In embodiments, the low profile base 1002 is configured to be inserted and/or built into a shoe or sandal like apparatus. Accordingly, the low profile base 1002 can be configured as a mid-sole or layer between the insole and/or platform 1004, or configured as a portion of an outsole in direct contact with the ground. Accordingly, the low profile base has a thickness of about 1 mm to about 10 cm, and in particular embodiments about 5 mm. Accordingly, the low profile base 1002 may be made out of any material suitable for supporting the weight of a user standing thereon, including but not limited to rubber, polymer, foam, plastic, thermoplastic, cork or similar material and/or combinations thereof.

In embodiments, the first magnetic layer 1006*a* below first elastic layer 1010 includes static magnetic field generating devices, such as permanent Ferro-magnets, but may also include electromagnets, coils, or dynamic magnetic field generating devices. In embodiments, the first magnetic layer 1006*a* is made of any suitable magnetic material such as one or more static ferromagnetic objects, electromagnets, flexible magnets, injection molded magnets, neodymium iron boron magnets, samarium cobalt magnets, alnico magnets, ceramic magnets, or combinations thereof. In one particular embodiment, first magnetic layer 1006*a* is a flexible magnet configured to cover the underside of the first elastic layer 1010. In embodiments, the first magnetic layer 1006*a* can have a thickness of about 1 mm to about 5 cm.

The second magnetic layer 1006*b*, can be a set of electromagnets, coils, or other dynamic magnetic field generating devices. In embodiments, the second magnetic layer 1006*b*, can be one or more static or dynamic ferromagnetic objects, electromagnets, flexible magnets, injection molded magnets, neodymium iron boron magnets, samarium cobalt magnets, alnico magnets, ceramic magnets, or combinations thereof. In one particular embodiment, second magnetic layer 1006*b* is a flexible magnet configured to coat or cover the low platform base 1002. In embodiments, the second magnetic layer can have a thickness of about 1 mm to about 5 cm.

By varying the field intensity and/or alternating the polarity of the second magnetic layer 1006*b* a vertical vibration of the platform 1004 can be induced. The vibrational frequency is determined by the rate of change of the magnetic properties, while the amplitude of the vibration is determined by the magnetic field intensity. Additionally, the magnetic field intensity may be increased or decreased as needed, depending on a patient's weight, to properly position and vibrate the platform 1004. In embodiments, platform 1004 vibrates vertically with a frequency of between 0 Hz and 10 KHz.

First elastic layer 1010 is configured to create support and fit within system 1000. The first elastic layer 1010 can be any elastomeric material such as rubber, cloth/rubber combinations, or soft elastic material, such as foamed polyurethane (PU). The first elastic layer 1010 may have a suitable density, so that it is readily deformed when being squeezed and able to recover quickly and freely from squeezing. The main body of the first elastic layer 1010 may have an overall height or size properly decided depending on a use intended for it. For example, it may be 1 mm to 5 cm in height for suitably positioning in system 1000.

Figure 10B:
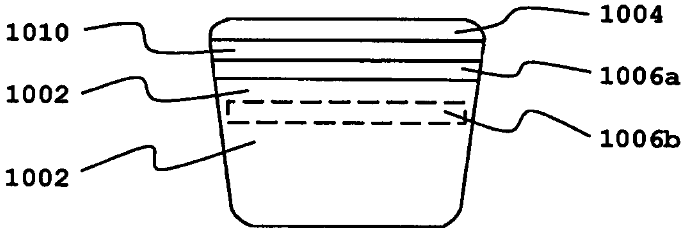
FIG. 10B is front schematic view of the same embodiment.

Referring now to FIG. 10B a front profile view of the apparatus of FIG. 10A is shown. The system 1000 includes a platform 1004 configured as an insole or the exterior portion of the device located directly beneath the foot of a user (not shown in FIG. 10B). The platform 1004 is disposed upon a first elastic layer 1010. Two magnetic layers 1006*a* and 1006*b* are positioned, first magnetic layer 1006*a*, on the underside of the first elastic layer 1010 and, a second magnetic layer 1006*b*, within the low profile base 1002, such that the first magnetic layer 1006*a* and the second magnetic layer 1006*b* are paired.

Figure 10C:
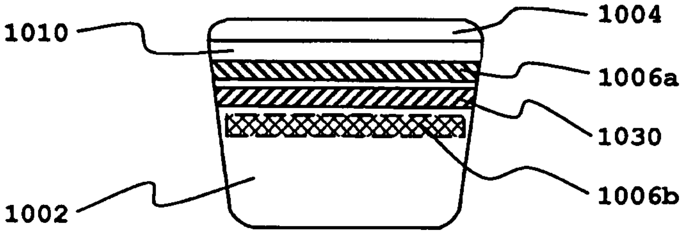
FIG. 10C is a schematic view of another alternate embodiment of a low profile vibrating plate in accordance with the present disclosure.

Optionally, as best shown in FIG. 10C, a second elastic layer 1030 may be coated upon the second magnetic layer 1006*b* within the low profile base 1002. The second elastic layer can be any elastomeric material such as rubber, cloth/rubber combinations, or soft elastic material, such as foamed polyurethane (PU). In embodiments, the elastic layer is made of material that does not inhibit the passage of a magnetic field there through. The second elastic layer may have a suitable density, so that it is readily deformed when being squeezed and able to recover quickly and freely from squeezing. The main body of the second elastic layer may have an overall height or size properly decided depending on a use intended for it. For example, it may be 1 mm to 5 cm in height for suitably positioning in system 1000.

Figure 11A:
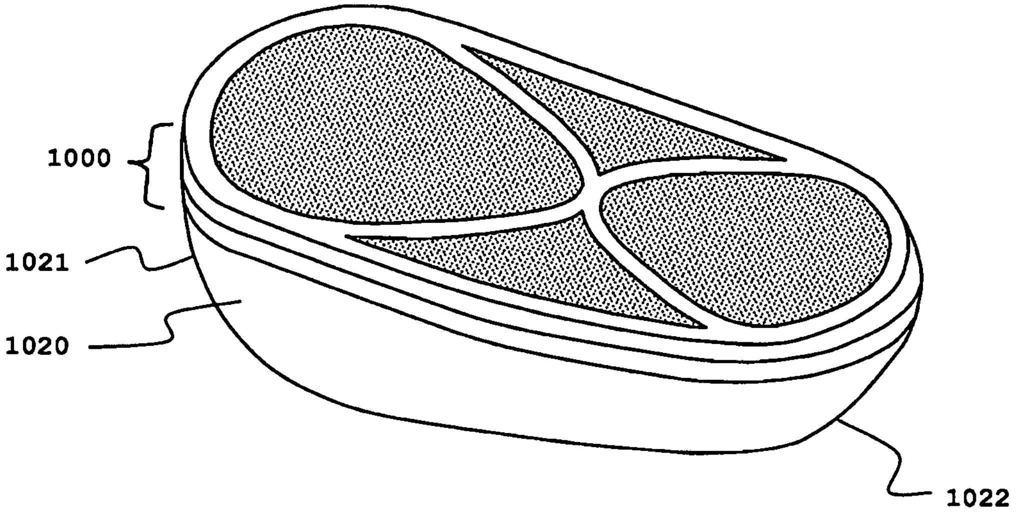
FIG. 11A is a schematic view of another alternate embodiment of a low profile vibrating plate in accordance with the present disclosure.
Figure 11B:
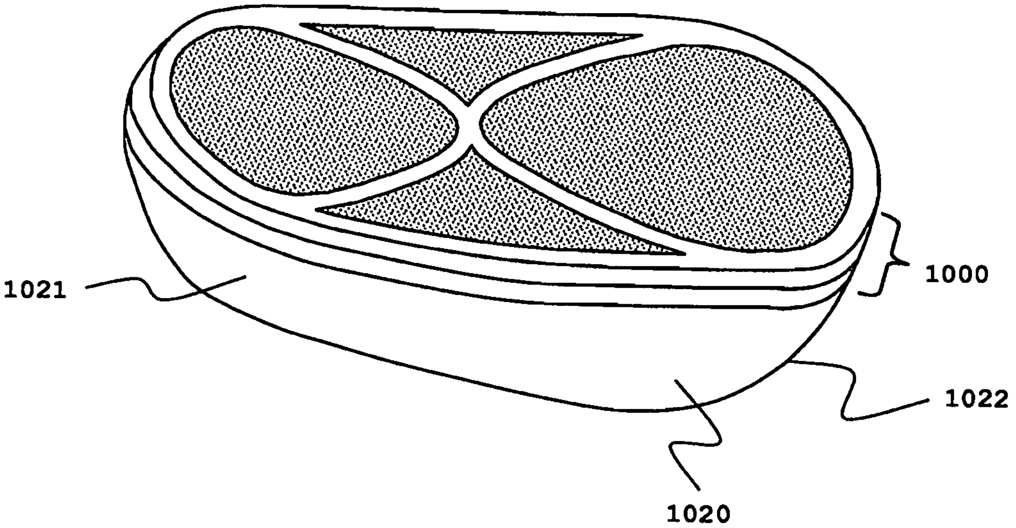
FIG. 11B is a schematic view of another alternate embodiment of a low profile vibrating plate in accordance with the present disclosure.

Referring now to FIG. 11A, system 1000 of FIGS. 10A and 10B are shown. The apparatus is shaped so that it is usable for the left or right foot of a user and accommodates numerous foot sizes. For example, system 1000 is long enough to accommodate the foot of a large adult male having a foot length of about 24 cm to about 30 cm, a small child having a foot length of about 14 cm to about 20 cm, and various lengths therebetween. The surface of the platform 1004 is textured. In embodiments, system 1000 can be combined with a base 1020 which connects to the underside of the system 1000. Here, base 1020 is in the shape of a wedge suitable for floor applications. As shown in FIG. 11A the distal end 1021 of the base 1020 is higher than the proximal end 1022, so that the heal of the user will be lower than the toes of the user. Referring now to FIG. 11B, system 1000 is shown disposed upon base 1020 such that the distal end 1021 is lower than the proximal end 1022, so that the heal of the user is elevated above the toes of a user. Accordingly, vibrations can be applied to feet in the fetal position.

Base 1020 can have a variety of shapes and made of a variety of materials such as plastic, thermoplastic, polymer, rubber, cork, wood, and other materials known in the art. The base 1020 material should be stiff enough and durable enough to withstand the weight of the user after numerous uses where a user is standing on the system 1000 disposed upon the base 1020.

Figure 12A:
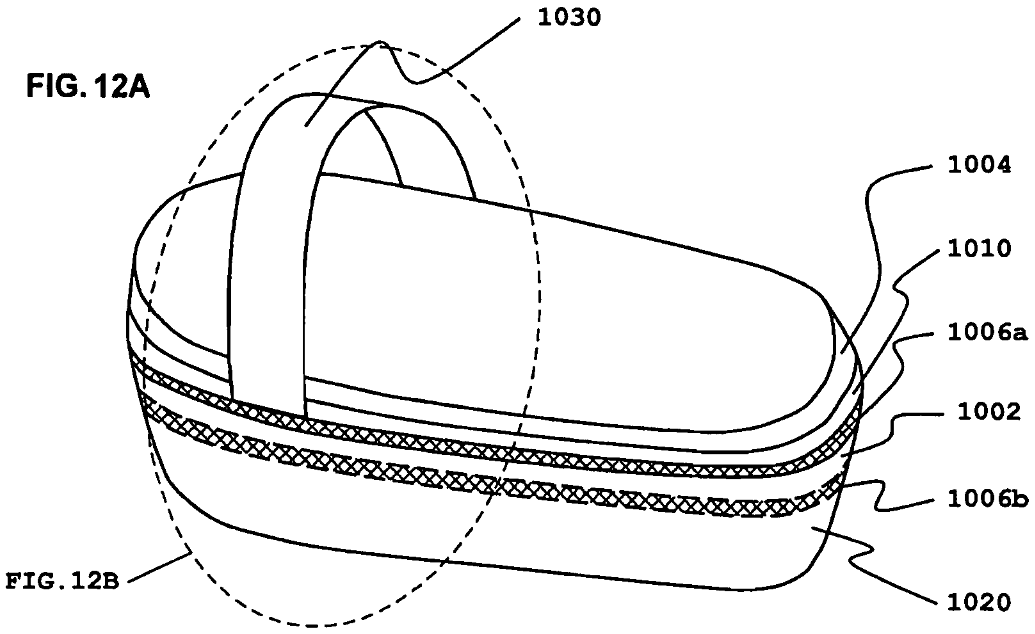
FIG. 12A is a schematic view of another alternate embodiment of a low profile vibrating plate in accordance with the present disclosure.

Referring now to FIG. 12A, an alternative wearable embodiment is shown having base 1020. Base 1020 can be an outsole attachment, or portion of the apparatus that touches the ground when worn by a user. In embodiments, base 1020 is shaped to form a heel, which may be a single or a separate piece of the outsole. Base 1020 can be made out of stiff materials such as plastic, rubber, or polymer, Kevlar, cork, or other materials known in the art. In embodiments, base 1020 is replaceable.

Figure 12B:
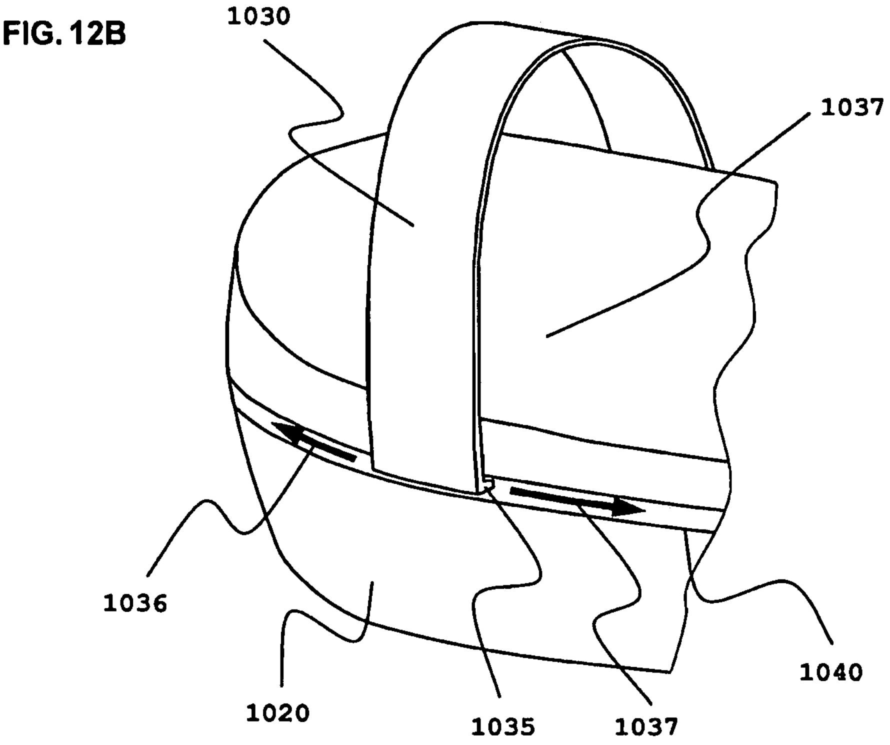
FIG. 12B is a greatly enlarged schematic view of the upper or vamp connecting to the body of the low profile vibrating plate in accordance with FIG. 12A.

Still referring to FIG. 12A, an alternative embodiment is shown having a vamp or upper 1030. Vamp or upper 1030 separates the foot of the user from the air, helps hold the apparatus on the foot, and/or counters the load applied to the foot from the vibrations of the platform 1004. Here, vamp or upper 1030 is designed to cover the toes or top of the foot similar to a sandal or flip-flop style footwear. Referring to FIG. 12B, an enlarged view of the upper 1030 of FIG. 12A is shown connected to the system 1000 by an adjustable track system. Here, the outer edges 1035 of the upper 1030 snap into, or are otherwise set within the track 1040. It is envisioned that the track system is adjustable so a user may push the vamp 1030 distally away from the leg in the direction of arrow 1036, or proximally towards the leg in the direction of arrow 1037 to ensure a snug and/or comfortable fit. Accordingly, in some methods of use, the user wearing the device in accordance with the present disclosure can vertically position the device during supine applications.

Figure 13:
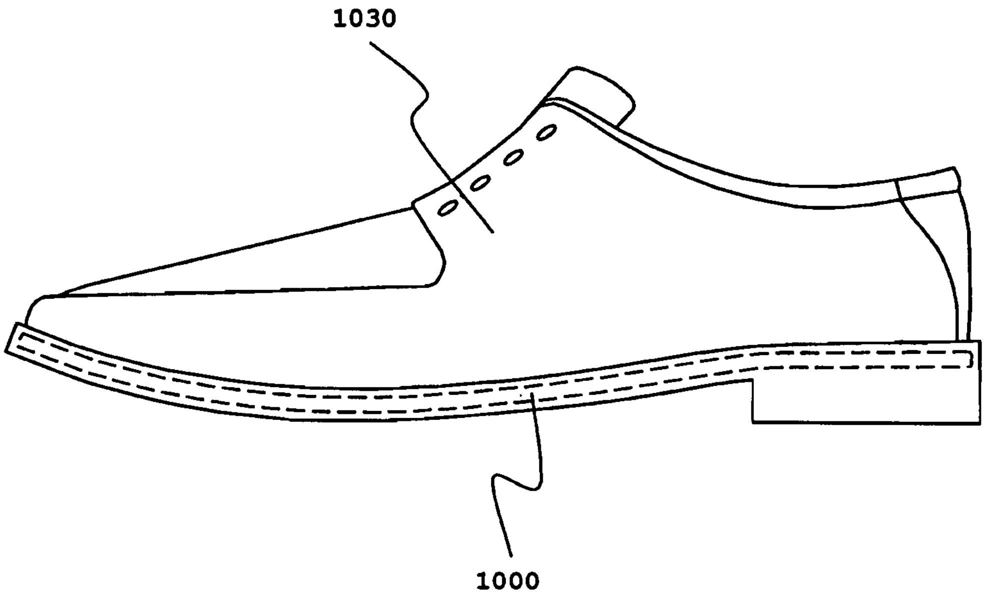
FIG. 13 is a schematic view of another alternate embodiment of a low profile vibrating plate in accordance with the present disclosure.

Referring to FIG. 13, upper or vamp 1030 is shown as a shoe. System 1000 is wearable and disposed upon, or incorporated into the insole of the shoe. The body of the shoe or vamp holds the device against the foot during vibrational applications.

The following non-limiting prophetic examples further illustrate methods in accordance with this disclosure.

Example 1

A 52 year old woman is suffering from deep vein thrombosis (DVT) in her left calf. A vibrating plate suitable for treatment of deep vein thrombosis (DVT) is routinely applied to her calf twice daily. The plate vibrates against the calf at a frequency of about 30 KHz for 10 minutes per application. Blood flow throughout the calf is increased.

Example 2

A 45 year old man is suffering from deep vein thrombosis (DVT) in his right leg. A vibrating plate in accordance with the present disclosure and suitable for treatment of deep vein thrombosis (DVT) is routinely applied to the bottom of his right foot three times a day. The plate vibrates against the foot at a frequency of about 30 KHz for 5 minutes per application. Blood flow throughout the right leg is increased.

Example 3

A 55 year old man is suffering from orthostatic intolerance. While sitting, a vibrating plate in accordance with the present disclosure is routinely applied to the bottom of his right and left feet three times a day. The plate vibrates against the feet at a frequency of about 30 KHz for 5 minutes per application. Blood flow throughout both legs is increased, and orthostatic intolerance subsides.

Example 4

A 75 year old woman is suffering from vascular disease, namely peripheral venous disease. Blood flow throughout her legs is poor. While sitting, a vibrating plate in accordance with the present disclosure is routinely applied to the bottom of her feet four times a day. The plate vibrates against the feet at a frequency of about 25 KHz for 10 minutes per application. Blood flow throughout both legs is increased, and peripheral venous disease is alleviated.

Example 5

A 45 year old woman is suffering from vascular disease, namely peripheral venous disease. Blood flow throughout her legs is poor. While sitting in the passenger seat of a car and commuting to work she rests her feet on a vibrating plate in accordance with the present disclosure. The plate vibrates against the feet at a frequency of about 30 Hz for 20 minutes while she commutes to work. Blood flow throughout both legs is increased, and peripheral venous disease is alleviated.

Example 6

A 45 year old man is suffering from deep vein thrombosis (DVT) in his right leg. Three times a day the man places his foot into an apparatus in accordance with the present disclosure by placing his toes under an upper and activating the device. The system vibrates and treats the deep vein thrombosis (DVT) The plate vibrates against the foot at a frequency of about 30 KHz for 5 minutes per application. Blood flow throughout the right leg is increased. Incidence if DVT is decreased.

Example 7

A 55 year old man is suffering from deep vein thrombosis (DVT) in his right and left leg. Three times a day the man places his foot into two socks, each sock containing a device in accordance with the present disclosure at the bottom. The devices vibrate and treat the deep vein thrombosis (DVT) The plates vibrate against the feet at a frequency of about 30 Hz for 5 minutes per application. Blood flow throughout both the right leg and left leg is increased. Incidence if DVT in both legs is decreased.

The described embodiments of the present disclosure are intended to be illustrative rather than restrictive, and are not intended to represent every embodiment of the present disclosure. Various modifications and variations can be made without departing from the spirit or scope of the present disclosure as set forth in the following claims both literally and in equivalents recognized in law.

What is claimed is:

1. A wearable apparatus for treating tissue ailments comprising:

a low profile base, a platform movably connected to said low profile base in spaced relation thereto, a first magnetic layer interconnected to said platform and at least partially movable therewith, a second magnetic layer interconnected to said low profile base in substantially aligned relation to said first magnetic layer, said first and second magnetic layers comprising equivalent polarities resulting in a repellent force being developed therebetween, at least said second magnetic layer comprising adjustable magnetic properties to impart vibratory movement to said first magnetic layer and said platform, and said platform and said low profile base cooperatively structured to at least partially define footwear.

2. An apparatus according to claim 1, wherein the apparatus is shaped to fit within a shoe or sandal.

3. An apparatus according to claim 1, wherein the apparatus is incorporated into the body of a shoe or sandal.

4. An apparatus according to claim 1 comprising a vamp.

5. An apparatus according to claim 4, wherein the vamp has a first end and a second end, and both ends are adjustably disposed within a track on the base of the apparatus.

6. An apparatus according to claim 4, wherein the vamp is adjustable along the length of the apparatus.

7. An apparatus according to claim 1, wherein the upper portion of the platform is textured.

8. An apparatus according to claim 1, wherein said platform and said base are collectively disposed within the insole of a shoe.

9. An apparatus according to claim 1, wherein said platform vibrates vertically with a frequency of between 0 Hz and 10 KHz.

10. An apparatus according to claim 1, wherein said platform vibrates horizontally with a frequency of between 0 Hz and 10 KHz.

11. An apparatus according to claim 1 further comprising a controller disposed in electrical communication with said second magnetic layer and structured to control said adjustable magnetic properties including said polarity and magnetic field intensity of said second magnetic layer.

12. An apparatus according to claim 11, wherein said first magnetic layer includes one or more static ferromagnetic objects, electromagnets, flexible magnets, injection molded magnets, neodymium iron boron magnets, samarium cobalt magnets, alnico magnets, ceramic magnets, or combinations thereof.

13. An apparatus according to claim 1, wherein said first magnetic layer is configured to generate a static magnetic field and said adjustable magnetic properties of said second magnetic layer are structured to generate a dynamic magnetic field, having any combination of alternating polarities and varying magnetic field intensities.

14. An apparatus according to claim 1, wherein said platform vibrates vertically a distance of about 1 micrometer to about 40 micrometers.

15. An apparatus according to claim 1, wherein said platform vibrates horizontally a distance of about 1 micrometer to about 40 micrometers.

16. An apparatus according to claim 1, comprising a first elastic layer disposed in interconnecting relation between the first magnetic layer and the platform.

17. An apparatus according to claim 16, comprising a second elastic layer positioned between the second magnetic layer and the first magnetic layer.

18. An apparatus according to claim 1 further comprising a third magnetic layer disposed upon the platform, and a fourth magnetic layer disposed upon the low profile base.

19. An apparatus according to claim 18 wherein said third magnetic layer is configured to generate a static magnetic field and said fourth magnetic layer is configured to generate a dynamic magnetic field, having any combination of alternating polarities and varying magnetic field intensities.

20. An apparatus according to claim 1, further comprising one or more stops configured to restrict movement of the platform within a predefined displacement range.

21. A wearable apparatus as recited in claim 1 wherein said platform and said low profile base are further cooperatively structured to support at least a partial weight of an individual.

22. A wearable apparatus for treating tissue ailments comprising:

a low profile base;

a platform movably disposed in juxtaposed alignment with said low profile base, said platform having an upper portion and a lower portion;

a first magnetic layer interconnected to said platform and movable therewith, said first magnetic layer extending substantially along the length of a dimension of the platform, a second magnetic layer disposed upon said base in aligned relation with the first magnetic layer, wherein the polarity of the first magnetic layer is substantially equal to the polarity of the second magnetic layer such that the first magnetic layer and the second magnetic layer repel one another;

a first elastic layer positioned in interconnecting relation between the first magnetic layer and the platform;

a controller disposed in electrical communication with said second magnetic layer and configured for control of polarity and magnetic field intensity of said second magnetic layer, and said platform and said base cooperatively structured to at least partially define footwear and to support at least a partial weight of an individual.

23. An apparatus according to claim 22, comprising a second elastic layer positioned between the second magnetic layer and the first magnetic layer.

24. An apparatus according to claim 22, wherein said apparatus is configured to be incorporated into a shoe or sandal.

* * * * *